US009849435B2

(12) United States Patent
Rotello et al.

(10) Patent No.: US 9,849,435 B2
(45) Date of Patent: Dec. 26, 2017

(54) MALEIC ANHYDRIDE POLYMER-STABILIZED MICROCAPSULES

(71) Applicants: Firmenich SA, Geneva (CH); UNIVERSITY OF MASSACHUSETTS, Boston, MA (US)

(72) Inventors: Vincent M. Rotello, Amherst, MA (US); Bradley P. Duncan, Sunderland, MA (US); Valery Normand, Plainsboro, NJ (US); Huda Jerri, Plainsboro, NJ (US); Lahoussine Ouali, Geneva (CH); Daniel Benczedi, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/105,487

(22) PCT Filed: Dec. 18, 2014

(86) PCT No.: PCT/EP2014/078603
§ 371 (c)(1),
(2) Date: Jun. 16, 2016

(87) PCT Pub. No.: WO2015/091877
PCT Pub. Date: Jun. 25, 2015

(65) Prior Publication Data
US 2016/0317993 A1   Nov. 3, 2016

Related U.S. Application Data

(60) Provisional application No. 61/918,063, filed on Dec. 19, 2013.

(30) Foreign Application Priority Data

Jan. 7, 2014   (EP) .................................... 14150292

(51) Int. Cl.
*A01N 25/28* (2006.01)
*B01J 13/06* (2006.01)
(Continued)

(52) U.S. Cl.
CPC .............. *B01J 13/06* (2013.01); *A01N 25/08* (2013.01); *A61K 8/11* (2013.01); *A61K 8/25* (2013.01);
(Continued)

(58) Field of Classification Search
CPC ............ A01N 25/28; B01J 13/14; B01J 13/04
See application file for complete search history.

(56) References Cited

U.S. PATENT DOCUMENTS

2007/0202063 A1   8/2007   Dihora et al.

FOREIGN PATENT DOCUMENTS

| EP | 1 741 775 A1 | 1/2007 |
| GB | 2 432 843 A | 6/2007 |

(Continued)

OTHER PUBLICATIONS

International Search Report and Written Opinion, Appl. No. PCT/EP2014/078603, dated Mar. 20, 2015.

*Primary Examiner* — Carlos Azpuru
(74) *Attorney, Agent, or Firm* — Winston & Strawn LLP (57) ABSTRACT

The present invention relates to microcapsules with a core-shell or matrix morphology stabilized by cross-linked nanoparticles. A process for the preparation of said microcapsules comprising selecting internal crosslinking of a Pickering emulsion is also an object of the invention. Perfumed consumer products, in particular fine fragrance, home and personal care products are also part of the invention.

20 Claims, 7 Drawing Sheets

(51) Int. Cl.
*B01J 13/04* (2006.01)
*A01N 25/08* (2006.01)
*B01J 13/14* (2006.01)
*C11D 3/50* (2006.01)
*A61K 8/11* (2006.01)
*A61K 8/25* (2006.01)
*A61K 8/81* (2006.01)
*A61Q 5/02* (2006.01)
*A61Q 5/12* (2006.01)
*A61Q 13/00* (2006.01)
*A61Q 15/00* (2006.01)
*A61Q 19/00* (2006.01)
*A61Q 19/10* (2006.01)

(52) U.S. Cl.
CPC .............. *A61K 8/8164* (2013.01); *A61Q 5/02* (2013.01); *A61Q 5/12* (2013.01); *A61Q 13/00* (2013.01); *A61Q 15/00* (2013.01); *A61Q 19/007* (2013.01); *A61Q 19/10* (2013.01); *B01J 13/04* (2013.01); *B01J 13/14* (2013.01); *C11D 3/505* (2013.01)

(56) References Cited

FOREIGN PATENT DOCUMENTS

| | | |
|---|---|---|
| GB | 2 432 850 A | 6/2007 |
| GB | 2 432 851 A | 6/2007 |
| GB | 2 432 852 A | 6/2007 |
| WO | 03/097218 A1 | 11/2003 |
| WO | 2005/054422 A1 | 6/2005 |
| WO | 2007/062733 A1 | 6/2007 |
| WO | 2007/062833 A1 | 6/2007 |
| WO | 2008/016684 A1 | 2/2008 |
| WO | 2008/065563 A1 | 6/2008 |
| WO | 2009063257 * | 5/2009 |
| WO | 2011/154893 A1 | 12/2011 |
| WO | 2013/182855 A2 | 12/2013 |

* cited by examiner

MALEIC ANHYDRIDE POLYMER-STABILIZED MICROCAPSULES

This application is a 371 filing of International Patent Application no. PCT/EP2014/078603 filed 18 Dec. 2014, which claims the benefit of U.S. provisional patent application No. 61/918,063 filed 19 Dec. 2013 and European patent application no. 14150292.2 filed 7 Jan. 2014.

TECHNICAL FIELD

The present invention relates to a process for the preparation of microcapsules stabilized by inorganic particles that are selectively internally crosslinked, as well as capsules obtained by said process. Consumer products comprising said capsules, in particular products with high levels of ethanol or liquid aqueous surfactant-rich consumer products are also part of the invention.

BACKGROUND OF THE INVENTION

One of the problems faced by the perfumery industry lies in the relatively rapid loss of olfactive benefit provided by odoriferous compounds due to their volatility, particularly that of "top-notes". In order to tailor the release rates of volatiles, delivery systems such as microcapsules containing a perfume, are needed to protect and later release the core payload when triggered. A key requirement from the industry regarding these systems is to survive suspension in challenging bases without physically dissociating or degrading. For instance, fragranced personal and household cleansers containing high levels of aggressive surfactant detergents are very challenging for the stability of microcapsules. On the other hand, fine fragrance formulations containing up to 90% ethanol, result in similar phenomena of destabilization and dissociation albeit by different mechanisms, of encapsulated systems added therein.

Aminoplast microcapsules formed of a melamine-formaldehyde resin have been largely used to encapsulate hydrophobic actives, thus protecting said actives and providing their controlled release. However, capsules such as aminoplast ones suffer from stability problems when used in consumer products comprising surfactants, such as perfumery consumer products, especially after prolonged storage at elevated temperatures. In such products, even though the capsule wall remains intact, the encapsulated active tends to leak out of the capsule by diffusion through the wall due to the presence of surfactants that are able to solubilise the encapsulated active in the product base. The leakage phenomenon reduces the efficiency of the capsules to protect the active and provide its controlled release.

A variety of strategies have been described to improve the stability microcapsules with oil core. Crosslinking of capsule walls, with chemical groups such as poly(amines) and poly(isocyanates), has been described as a way to improve stability of microcapsules. WO2011/154893 discloses for instance a process for the preparation of polyurea microcapsules using a combination of aromatic and aliphatic polyisocyanates in specific relative concentrations.

As an alternative to encapsulation, stabilization of oil/water interfaces with inorganic particles has been described in so-called Pickering emulsions. In this context, functionalization of inorganic particles to allow their crosslinking is known. For instance, Pickering emulsions crosslinked from an outer water phase with polyelectrolytes providing electrostatic interactions have been the object of prior disclosures. However, such systems are very likely to dissociate in a surfactant base or in ethanol over time as electrostatic interactions are insufficient to promote stability. Covalent crosslinking has also been described in relation with Pickering emulsion in the preparation of colloidosomes. In particular, the use of diisocyanates as crosslinker has been disclosed in scientific publications. WO2009/063257 also describes the use of polyisocyanates as possible crosslinker for surface-modified inorganic particles in order to prepare microcapsules with increased level of protection from u.v. light for the contents. These products are typically intended for agrochemical applications.

One of the major hurdles in using particle-stabilized capsules for perfume encapsulation intended for fine fragrance and other scented consumer product applications is their inherent instability to ethanol and the ability of surfactant molecules to readily displace particles from oil/water interface of emulsions.

Therefore there is still a need to develop improved delivery systems that efficiently protect and then release, when needed, an active ingredient such as a perfume oil, while surviving suspension in challenging bases without physically dissociating or degrading. A particular need exists in the case of fragranced personal and household cleansers containing high levels of aggressive surfactant detergents and fine fragrance formulations containing up to 90% ethanol. It is an object of the invention to provide such improved delivery systems.

SUMMARY OF THE INVENTION

In a first aspect, the present invention relates to a particle-stabilized microcapsule obtainable by a process comprising the steps of suspending inorganic solid particles with at least one amine functionality in water to form an aqueous phase; suspending at least one maleic anhydride-containing polymer in a perfume or flavour oil to form an oil phase; and finally adding the oil phase to the water phase and mixing the resulting emulsion to form a core-shell or matrix structure with crosslinked particles present at the oil/water interface.

In a second aspect, the invention concerns a process for the preparation of those capsules as well as perfuming compositions and perfumed articles containing them, in particular compositions with high levels of ethanol on the one hand and consumer products with high levels of surfactants on the other hand.

DETAILED DESCRIPTION OF THE INVENTION

Unless stated otherwise, % are meant to designate percent by weight of a composition.

By inorganic particles with at least one amine functionality it is meant that each nanoparticle has been functionalised so as to comprise at least one amine moiety such as $NH_2$.

By "selectively crosslinked nanoparticles" it is meant that the functionalized particles interact explicitly with the crosslinker added to the oil core such that the particles are bound together but the oil core is not entirely polymerized to form a solid core.

By "maleic anhydride-containing polymer" it is meant that the polymer comprises maleic anhydride groups which react with amino groups to covalently bond the functionalized particles.

By "perfume or flavour oil", it is meant a single perfuming or flavouring compound or a mixture of several perfuming or flavouring compounds.

"Matrix" type morphology used in the context of the invention by opposition to "core-shell" morphology is also referred to as a composite structure and is meant to designate a network composite by opposition to a reservoir system, which nevertheless preserve the discrete microparticle morphology generated by the emulsion process. The configuration depends on the selection of maleic anhydride containing polymer.

The present invention relates to a robust yet permeable vehicle for an active ingredient e.g. perfume oil, particularly adapted in the case of perfume, to fine fragrance applications. In particular, a first object of the present invention consists of a particle-stabilized microcapsule obtainable by a process comprising the steps of:
1) Suspending inorganic solid particles with at least one amine functionality in water, to form an aqueous phase;
2) Suspending at least one maleic anhydride-containing polymer in a perfume or flavour oil to form an oil phase;
3) Adding the oil phase to the water phase and mixing the resulting emulsion to form a microcapsule with crosslinked particles present at the oil/water interface.

Figure 1:
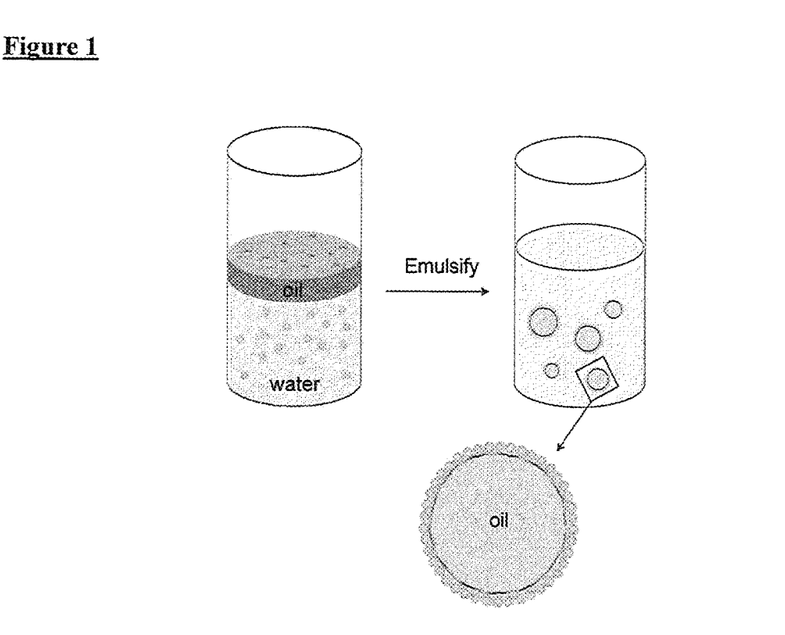
FIG. 1: shows a schematic representation of the formation of a crosslinked capsule with core-shell morphology.
Figure 4:
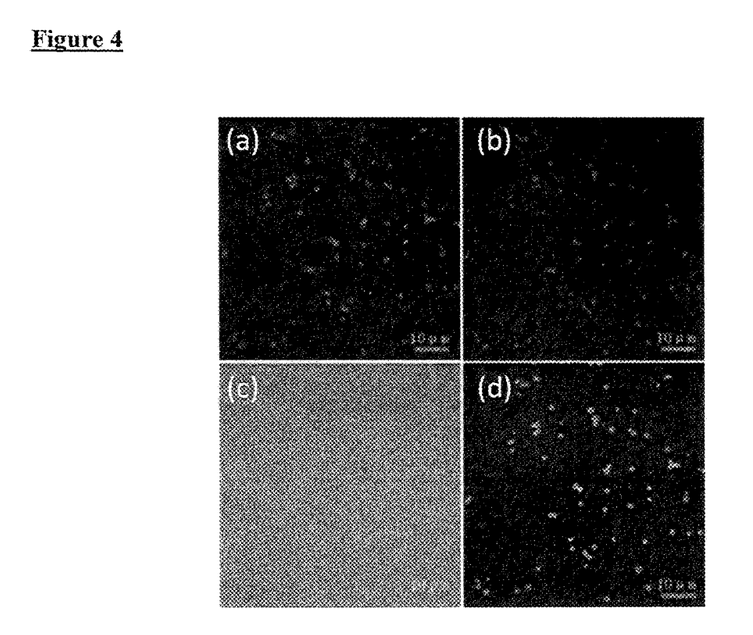
FIG. 4: shows confocal images of fluorescently labelled particles and oil forming a core-shell structure after crosslinking. The four quadrants of the image correspond to the (a) FITC-labelled crosslinked silica particle shells appearing as rings in the image, (b) oil phase containing the crosslinking polymer and Nile red fluorophore (c) bright field image and (d) overlay with the crosslinked nanoparticle shell encapsulating the red oil core forming a core-shell structure.
Figure 6:
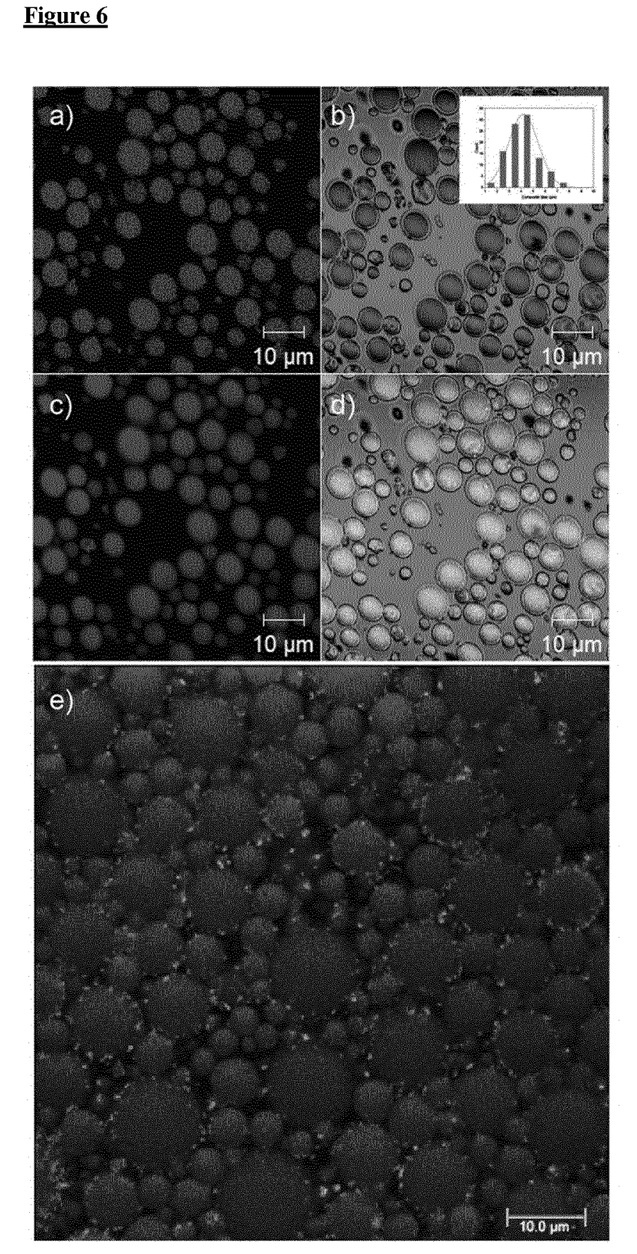
FIG. 6: shows confocal images of FITC-labelled particles with Nile red-loaded oil to form crosslinked composite structures (6a-d) compared to an uncrosslinked core-shell control (e). The quadrants correspond to the (a) FITC-labelled silica particles throughout the composite composition, (b) oil phase containing the crosslinking polymer and Nile red fluorophore (c) bright field image and (d) overlay of the co-localized green fluorescent nanoparticles with the fluorescent oil core. The inset shows composite size distribution.
Figure 7:
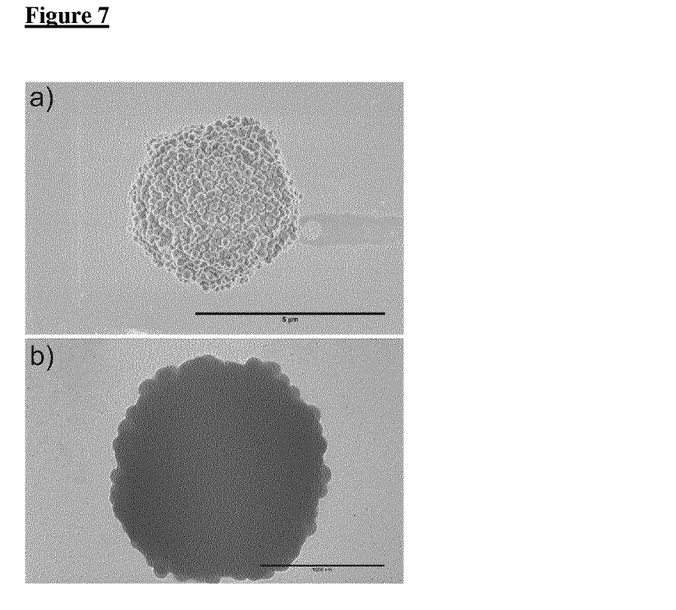
FIG. 7: illustrates the physical structure and presence of particles at the surface of internally-crosslinked composite microcapsules as analyzed using TEM after drying from ethanol solution.

The morphology of the microcapsules of the invention can vary from core-shell type to a matrix type depending on kinetics and thermodynamics in the preparation process. According to a first embodiment, the capsules of the present invention have a core-shell structure with the particles present at the oil/water interface. This schematic is given in FIG. 1, and the structure is illustrated in FIG. 4 wherein nanoparticles are stained using FITC-green (excitation wavelength=490 nm emission wavelength=525 nm) and the oil was stained using Nile red fluorophore (excitation wavelength=515 nm, emission wavelength=525 nm). The bright green fluorescent shell in the upper left quadrant ($\lambda_{ex}$=488 nm) envelops the red fluorescent oil core in the upper right quadrant ($\lambda_{ex}$=514 nm), as clearly seen in the overlay image in the lower right quadrant of the image series. According to a second embodiment, the capsules of the present invention have a matrix structure. This schematic is given in FIG. 2 and the structure is represented in FIG. 6. Without being bound by theory it is believed that in that case, the crosslinking reaction simultaneously pulls the particles into the oil phase as the particle surface becomes more hydrophobic, generating an oil-containing composite structure with particles present at the outer surface as illustrated in FIG. 7.

The capsules of the invention are obtained through a process characterized by an internal cross linking with maleic anhydride-containing polymer of particle-stabilized oil droplets, which leads to successful encapsulation of volatile materials. The inorganic/organic hybrid system of amino-particles crosslinked by maleic anhydride-containing polymer shows remarkable retention of different encapsulated hydrophobic payloads without the need to post-functionalize or anneal the capsules after assembly. Furthermore, the use of biocompatible maleic anhydride-based polymers facilitates the incorporation of these delivery systems into a variety of complex, multicomponent consumer products. A robust, mechanically stable delivery system is therefore provided, which surprisingly and advantageously survives suspension in surfactant and also remains stable in the highly concentrated alcohol solvents used in fine fragrance without dissociating, dissolving or degrading. The remarkable physical stability to ethanol and surfactant molecules of the capsules of the invention in such products is unprecedented. Without wishing to be bound by theory, it is believed that the generated particle-stabilized capsules become robust through physical and chemical crosslinking by the specific polymer at the oil/water interface. In particular the use of the particular biocompatible polymer crosslinker allows overcoming previous issues of dissociation of the particle shells in challenging bases. The obtained polymer-particle shell provides an optimized protection for the internal core, and does so in a low cost and biocompatible way. Furthermore, the system is amenable to a wide variety of oil and requires low amount of processing.

Suitable inorganic particles according to the present invention includes silica, silicates, titanium dioxide, aluminium oxide, zinc oxide, iron oxide, mica, clays, kaolin, montmorillonite, laponite, bentonite, perlite, dolomite, diatomite, vermiculite, hectorite, gibbsite, illite, kaolinite, aluminosilicates, gypsum, bauxite, magnesite, talc, magnesium carbonate, calcium carbonate, and diatomaceous earth. Preferably, inorganic particles selected from the group consisting of cosmetic-grade oxides such as silicon dioxide, titanium dioxide and zinc oxide are used. More preferably silica is used. The size of the nanoparticles is typically comprised between 100 and 1000 nm, preferably between 100 to 500 nm.

Figure 8:
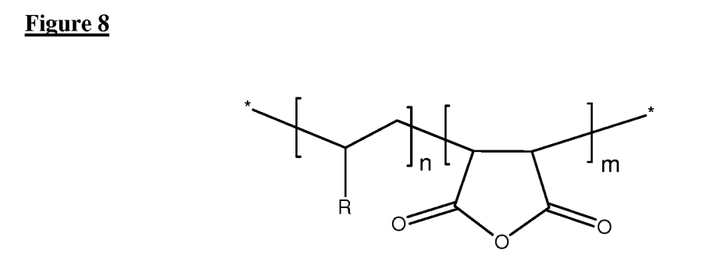
FIG. 8: shows a polymer structure with maleic anhydride monomer for crosslinking and variable hydrophobic R moiety

According to a preferred embodiment, inorganic particles are present in an amount comprised between 0.1 and 5 wt % of the aqueous phase. The maleic anhydride-containing polymer is an essential element of the present invention. This high molecular weight polymer with a long contour length proved to efficiently link particles together and form a tightly crosslinked polymer/particle hybrid membrane. The polymer is composed of two monomers, namely a hydrophobic moiety and a maleic anhydride moiety as illustrated in FIG. 8. Preferably, the hydrophobic moiety is selected from the group consisting of styrene, isoprene, ethylene, methyl vinyl ether, propylene and octadecene. These can be random, graft or alternating polymer. More preferably, the hydrophobic moiety consists of high molecular weight monomers. The maleic anhydride-containing polymer is typically present in an amount comprised between 1 and 20 wt % of the oil phase.

The particle-stabilized microcapsules of the invention may encapsulate a perfume or flavour oil as well as other active agents. Advantageously, oils that can be successfully encapsulated in the products of the invention have a wide range of hydrophobicities and volatilities. It is worth also mentioning that by "perfuming compound" it is meant here a compound, which is used in a perfuming preparation or a composition to impart a hedonic effect. In other words such compound, to be considered as being a perfuming one, must be recognized by a person skilled in the art as being able to impart or modify in a positive or pleasant way the odour of a composition, and not just as having an odour. The perfume oil can be a perfuming ingredient alone or a mixture of ingredients in the form of a perfuming composition. Any perfuming ingredient or composition can be used. Typically, perfume oil comprising at least one ingredient with a log P above 1 can be used in the present invention. Flavouring oils, i.e. one or several ingredients capable of imparting or modifying the taste of a composition or products are also suitable oil to be encapsulated in the products of the invention. Specific examples of such perfuming or flavouring ingredients may be found in the literature of reference, for example in Perfume and Flavour Chemicals, 1969 (and later editions), by S. Arctander, Montclair N.J. (USA), as well as in the numerous patent and other literature related to the perfume industry. They are well known to the skilled person in the art of perfuming consumer products, that is, or imparting a pleasant odour to a consumer product. The perfuming ingredients may be dissolved in a solvent of current use in the perfume industry. Examples of such solvents are diethyl phthalate, isopropyl myristate, Abalyn®, benzyl benzoate, ethyl citrate, limonene or other terpenes, or isoparaffins.

The invention further concerns a process comprising the steps of
1) Suspending inorganic solid particles with at least one amine functionality in water, to form an aqueous phase;
2) Suspending at least one maleic anhydride-containing polymer in a perfume oil to form an oil phase;
3) Adding the oil phase to the water phase and mixing to form a microcapsule with particles present at the oil/water interface.

The process of the invention consists in forming a Pickering emulsion that is further crosslinked from the inside-out. Water soluble, amine-functionalized particles stabilize the oil/water interface while poly(maleic) anhydride copolymers form covalent linkages between individual particles. Maleic anhydride-containing polymer advantageously allows to discriminately crosslink particles after the Pickering emulsion is to formed, rather than quickly reacting with all available particles to simply form particle aggregates in solution as was the case with known crosslinkers. Without wishing to be bound by theory, it is believed that maleic anhydrides open up to form amides and carboxylic acids so it could possibly form 2 bonds (di-amides) which could improve crosslinking efficiency.

Particles with amine functionality are in a first step of the process according to the invention suspended in an aqueous media. According to a particular embodiment, these solid particles are present in an amount comprised between 0.1 and 5 wt % of the aqueous phase. The pH of the aqueous phase is preferably adjusted between 7 and 11. Prior to mixing, at least one maleic anhydride containing polymer is suspended in a fragrance or flavour oil. This oil phase is then added to the aqueous phase and emulsified (see FIG. 1-2). In the process of the invention, the generated Pickering emulsion becomes further stabilized by the reaction of the particles' amine functionalities with the maleic anhydride moieties of the oil-soluble polymers (see FIG. 3). It is believed that the inside-out crosslinking advantageously prevents aggregation of multiple capsules and prevents coalescence of the oil droplets.

According to a particular embodiment, the capsules of the present invention comprise a core of hydrophobic perfume or flavour oil and a shell consisting of inorganic particles selectively cross linked with maleic anhydride-containing polymer. Those capsules provide surprisingly robust yet permeable vehicle for e.g. perfume oil, particularly adapted for perfumed consumer products. According to another embodiment, the capsules of the invention have a composite structure. Is it believed that during the process, hydrophilic amine-functionalized silica nanoparticles are assembled at the oil-water interface. Reaction of particles with a hydrophobic copolymer increases the hydrophobicity of the particles, resulting in particle migration into the oil phase and confining the covalent bond formation to the interior of the emulsions. These covalent linkages between particles and polymers induce a change in the configuration from a reservoir system to a network composite while preserving the discrete microparticle morphology generated by the emulsion process. These systems are also very robust and show substantial retention of hydrophobic payloads in the presence of ethanol.

A perfumed consumer product comprising the microcapsules of the invention is therefore also an object of the present invention. In particular this consumer product may be in the form of a home- or personal-care product or in the form of a fine fragrance product. Preferably, the consumer product comprises from 0.1 to 15 wt %, more preferably between 0.5 and 5 wt % of the microcapsules of the present invention, these percentages being defined by weight relative to the total weight of the consumer product. Of course the above concentrations may be adapted according to the olfactive effect desired in each product.

The capsules of the invention proved to be particularly useful in fine fragrance products where they demonstrated a surprising stability to ethanol. Another object of the invention therefore consists of a composition comprising up to 90 wt % of ethanol, e.g. from 10 to 90% and from 0.1 to 15 wt % of microcapsules are defined above. Preferably, said composition is in the form of a perfume, an eau de toilette, an eau-de-parfum, a Cologne, a body splash or spray or an after-shave lotion.

Examples of personal-care products include shampoos, hair conditioners, soaps, body washes such as shower gel, bubble bath or bath salts, mousses, oils or gels, hygiene products, cosmetic preparations, body lotions, deodorants and antiperspirants. Examples of home-care products include liquid detergents, all-purpose cleaners, fabric softeners and refreshers, ironing waters and detergents and softener. As detergents we include here products such as detergent compositions or cleaning products for washing up or for cleaning various surfaces, for example intended for the treatment of textiles or hard surfaces (floors, tiles, stone-floors etc.). The capsules of the invention are particularly and advantageously stable in liquid aqueous surfactant-rich consumer products. A liquid perfumed consumer product comprising from 2 to 50 wt % relative to the total weight of the consumer products of at least one surfactant, water and from 0.1 to 15 wt % of microcapsules as defined above is therefore another object of the invention.

Formulations of consumer products in which the microcapsules of the invention can be incorporated can be found in the abundant literature relative to such products. These formulations do not warrant a detailed description here which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO2008/016684, US2007/0202063, WO2007/062833, WO2007/062733, WO2005/054422, EP1741775, GB2432843, GB2432850, GB2432851 or in GB2432852.

The invention will now be further described by way of examples. It will be appreciated that the invention as claimed is not intended to be limited in any way by these examples.

EXAMPLES

Example 1

Silica-Stabilized Microcapsules
1.1 Synthesis and Functionalization of Silica Particles Silica particles were generated using an adapted Stober method, wherein 24 mL of ammonium hydroxide were added to 300 mL of absolute ethanol and stirred for five minutes in a 500 mL round bottom flask. 12 mL of tetraethyl orthosilicate were added to the reaction flask and stirred overnight at room temperature. 1.22 mL of 3-aminopropyl triethoxysilane were added to coat the nanoparticles and the reaction was allowed to stir for an additional 24 hours. The particles were purified by centrifuging and re-dispersing in water and ethanol (3× each). The silica particles were then dried and stored for use as the Pickering stabilizing particles.

1.2. Formation of Crosslinked Particles-Stabilized Capsules with a Core-Shell Morphology 0.2 g of the amino-functional silica generated as described above was suspended in 19.8 g of pH 10 deionized water to form a 1 wt % silica nanoparticle solution (aqueous phase). The particle solution was sonicated to hydrate and suspend the particles.

The oil phase was formed by dissolving 0.25 g of poly maleic anhydride containing polymer such as poly(stryrene-co-maleic anhydride) into 4.75 grams of limonene oil. The aqueous phase was homogenized together with the oil phase for 3 minutes to form crosslinked capsules.

Capsule Characterization

In order to confirm the formation of particle-stabilized emulsion droplets and visualize the assembly of fluorescent-core particles at the interface, confocal microscopy was used. Amine functionalized silica particles with a fluorescein isothiocyanate (FITC) core were used. An aqueous dispersion of these nanoparticles were emulsified with limonene containing the hydrophobic dye Nile red and poly maleic anhydride-containing polymer. FIG. 4 shows the capsules have a core shell structure with the particles located at the oil/water interface and the Nile red remaining in the hydrophobic core

Example 2

Silica-Stabilized Composite or Matrix Microcapsules

Figure 2:
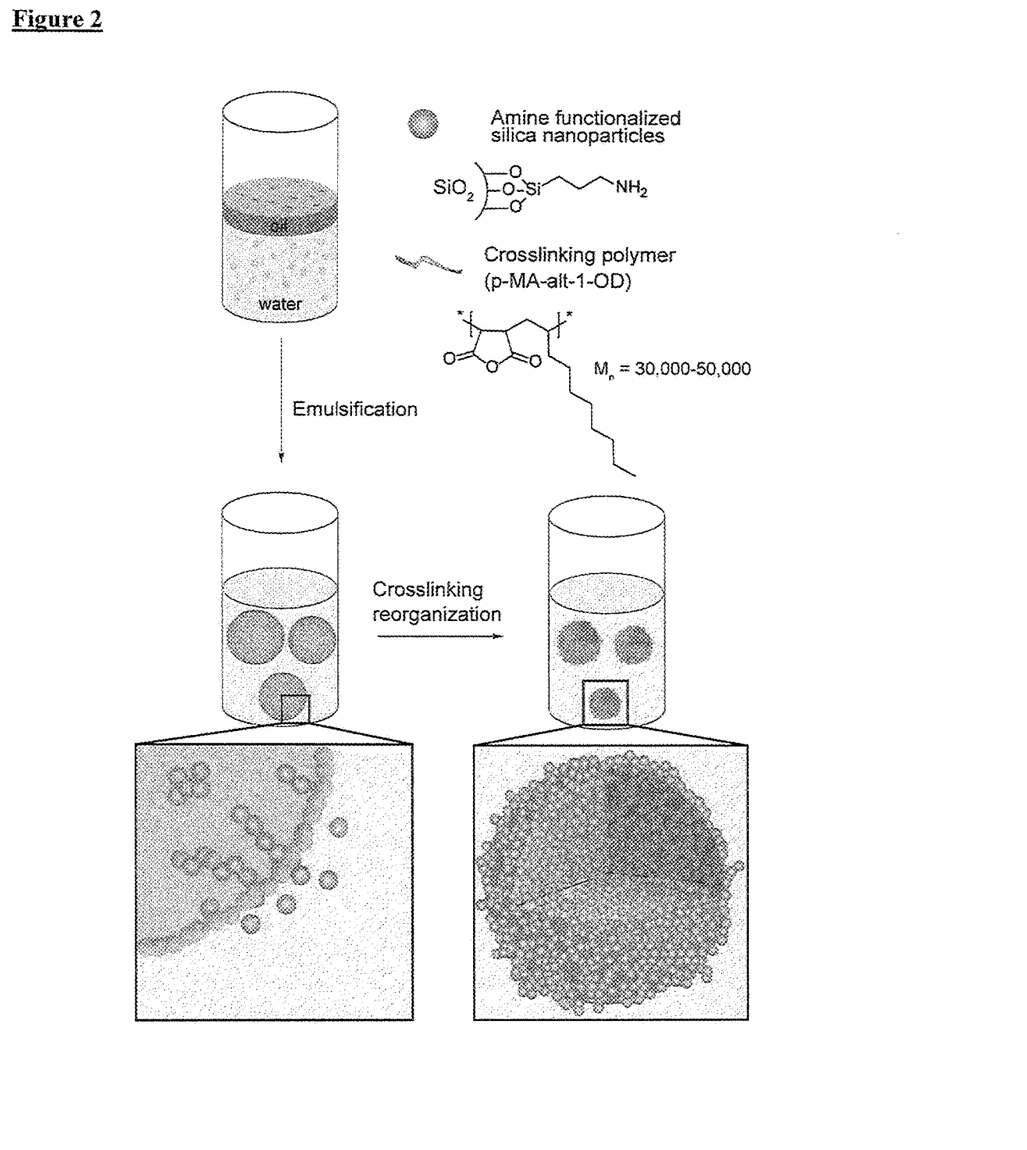
FIG. 2: shows a schematic representation of the formation of a crosslinked capsule with matrix morphology.
Figure 3:
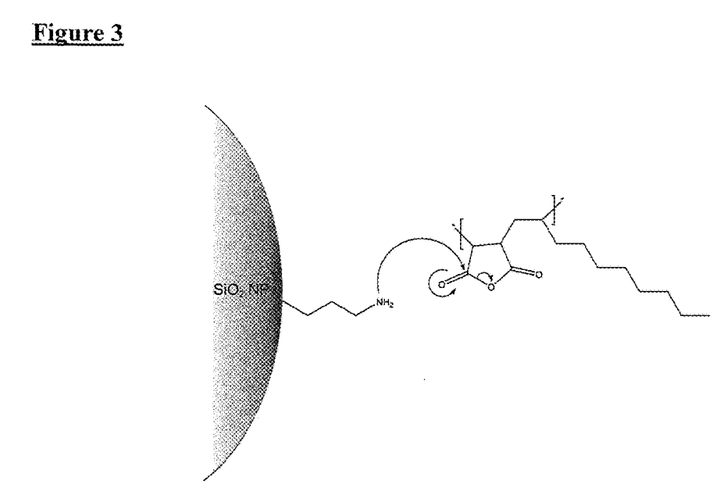
FIG. 3: illustrates the mechanism of covalent crosslinking between silica nanoparticles and maleic anhydride-containing polymer

Emulsions were generated according to the route described in FIG. 2. A hydrophobic polymer, Poly(maleic anhydride-alt-1-octadecene) (p-MA-alt-1-OD; average Mn of 30,000-50,000) purchased from Sigma-Aldrich was used and dissolved in limonene oil. Silica particles prepared according to Example 1 were suspended in Milli-Q water and the solution was adjusted to pH 10 with sodium hydroxide. The oil phase was added to the water phase and homogenized at 24,000 rpm for two minutes. Stable emulsions could be formed at silica loadings ranging from 0.6 to 2.0 wt %. Emulsions were then allowed to crosslink overnight at room temperature.

FIG. 6a-d shows the co-distribution of the particles and the Nile red containing oil phase, yielding matrix microcapsule morphologies. The average size of the generated composites (2 mL of 5 wt % p-MA-alt-1-OD in Nile red loaded limonene: 8 mL of 1.5 wt % silica particles in Milli-Q adjusted to pH 10) was 4.2±1.2 µm as determined using microscopy image analysis. As shown in FIG. 6e, control studies performed without the crosslinking polymer in the oil phase formed structures with a core-shell morphology. Nile red was not encapsulated effectively and polydisperse structures were formed for the control. Morphological stability of these cross-linked capsules were analyzed using SEM and TEM. A TEM image demonstrating the presence of particles at the surface of the crosslinked, composite microcapsules is provided in FIG. 7.

Example 3

Stability of Capsules According to the Invention in Ethanol Solution

Microcapsules prepared as described in Examples 1 and 2 were used for this stability test. Instead of Limonene, the following oils were individually encapsulated and tested:

TABLE 1

| Oil properties | | |
|---|---|---|
| Ingredient | Log P | Volatility (µg/L) |
| Limonene | 4.38 | 14183 |
| Phenylethyl Alcohol | 1.52 | |
| Applinate | 2.76 | 29820 |
| Delta-Damascone | 4.16 | 371 |
| Dihydromycenol | 3.47 | 1391 |
| β-Ionone | 3.012 | |

The capsules were incubated in a 80% ethanol and water solution, a common eau de toilette fine fragrance formulation, to test the stability of the capsules to dissociation.

Figure 5:
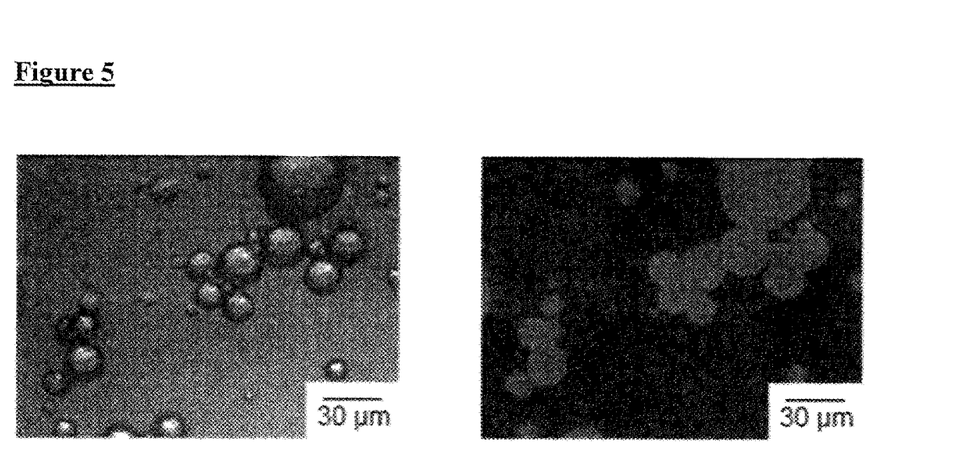
FIG. 5: shows brightfield and fluorescence images illustrating the physical stability and retention of Nile red fluorophore-loaded oil in crosslinked core-shell microcapsules after incubation in a 25% ethanol solution. Uncrosslinked systems dissociated completely when ethanol was added.

Both the core-shell microcapsules and matrix microcapsules were shown to be stable from pH 4 to pH 9 without physically dissociating, in addition to remaining physically intact and loaded with fragrance oil in concentrated ethanol solutions (25-80%). Loaded, crosslinked core-shell microcapsules from Example 1 are shown in FIG. 5 following incubation in 25% ethanol solution. Similar images were obtained for crosslinked, matrix-type microcapsules in 80% ethanol solutions. TEM and SEM images of dried, cross-linked microcapsules show structurally-intact spheres after incubation in 80% ethanol, as shown in FIG. 7a-b for the capsules from Example 2. Collapse of these capsules was not observed.

Example 4

Stability of Capsules in Ethanol Solution as a Function of Polymer Used

Figure 9:
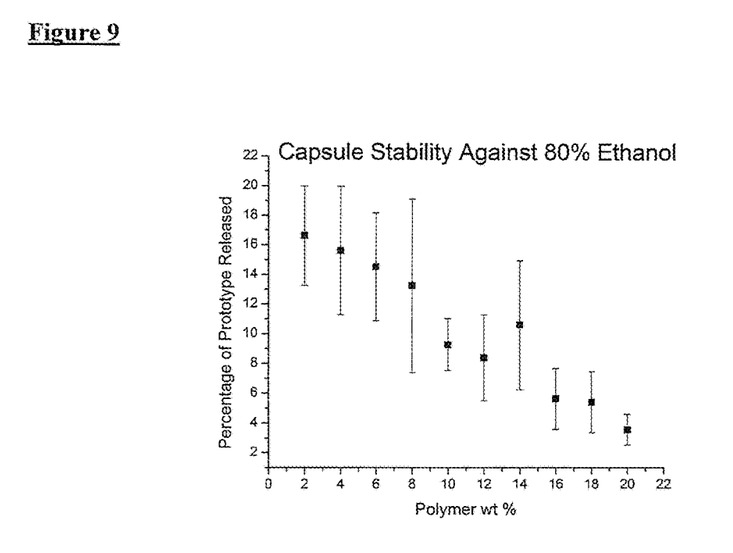
FIG. 9: illustrates the stability of the capsules of the invention to 80% ethanol solution as a function of dissolved polymer content in the internal phase.

Beta-ionone, a UV detectable oil, was encapsulated as described in Example 2, in order to quantify the release of oil from crosslinked capsules. The capsules were incubated in an 80% solution of ethanol. FIG. 9 shows increasing stability as the amount of polymer increases. As weight percentage of polymer in the oil phase increased the capsules displayed increased stability.

What is claimed is:

1. A particle-stabilized microcapsule obtainable by a process comprising the steps of:
   1) suspending inorganic solid particles with at least one amine functionality in water, to form an aqueous phase;
   2) suspending at least one maleic anhydride-containing polymer in a perfume or flavor oil to form an oil phase;
   3) adding the oil phase to the water phase and mixing the resulting emulsion to form the microcapsule due to reaction between the inorganic solid particles and the maleic anhydride-containing polymer with the resulting cross-linked particles present at the oil/water interface of the emulsion surrounding the perfume or flavor oil.

2. A microcapsule according to claim 1, wherein the inorganic particles are selected from the group consisting of silica, silicates, titanium dioxide, aluminium oxide, zinc oxide, iron oxide, mica, clays, kaolin, montmorillonite, laponite, bentonite, perlite, dolomite, diatomite, vermiculite, hectorite, gibbsite, illite, kaolinite, aluminosilicates, gypsum, bauxite, magnesite, talc, magnesium carbonate, calcium carbonate, and diatomaceous earth.

3. A microcapsule according to claim 2, wherein the inorganic particles comprise silica.

4. A particle-stabilized microcapsule obtainable by a process comprising the steps of:
   1) suspending inorganic solid particles with at least one amine functionality in water, to form an aqueous phase;
   2) suspending at least one maleic anhydride-containing polymer in a perfume or flavor oil to form an oil phase, wherein the at least one maleic anhydride-containing polymer is present in an amount comprised between 0.5 and 50 wt % of the oil phase; and
   adding the oil phase to the water phase and mixing the resulting emulsion to form a microcapsule with cross-linked particles present at the oil/water interface.

5. A microcapsule according to claim 4, wherein the at least one maleic anhydride-containing polymer is present in an amount comprised between 1 and 20 wt % of the oil phase.

6. A microcapsule according to claim 1, wherein the inorganic particles are present in an amount comprised between 0.1 and 5 wt % of the aqueous phase.

7. A microcapsule according to claim 1, wherein the size of inorganic, particles is comprised between 10 and 1000 nm.

8. A microcapsule according to claim 1, wherein the maleic anhydride-containing polymer comprises at least one hydrophobic moiety and at least one maleic anhydride moiety.

9. A microcapsule according to claim 8, wherein the hydrophobic moiety is selected from the group consisting of styrene, isoprene, ethylene, propylene, methyl vinyl ether, and octadecene.

10. A process for the preparation of a particle-stabilized microcapsule comprising the steps of:
    1) suspending inorganic solid particles with at least one amine functionality in water, to form an aqueous phase;
    2) suspending at least one maleic anhydride-containing polymer in a perfume oil to form an oil phase;
    3) adding the oil phase to the water phase and mixing to form the microcapsule due to reaction between the inorganic solid particles and the maleic anhydride-containing polymer with the resulting cross-linked particles present at the oil/water interface of the emulsion surrounding the perfume or flavor oil.

11. A composition comprising
    a) from 10 to 90 wt % of ethanol; and
    b) from 0.1 to 15 wt % of microcapsules as defined in claim 1.

12. A composition according to claim 11, in the form of a perfume, an eau de toilette, an eau de parfum, a cologne or a body splash or a spray.

13. A liquid perfumed consumer product comprising
    a) from 2 to 50% by weight, relative to the total weight of the consumer product, of at least one surfactant;
    b) water; and
    c) from 0.1 to 15% by weight of microcapsules as defined in claim 1.

14. A liquid perfumed consumer product according to claim 13, wherein said product is a home- or personal-care product.

15. A particle-stabilized microcapsule comprising
    a) a core of hydrophobic perfume or flavor; and
    b) a shell consisting of inorganic particles selectively cross-linked with a maleic anhydride-containing polymer.

16. A particle-stabilized microcapsule according to claim 1, wherein the cross-linked particles form a matrix structure.

17. The microcapsule of claim 1, which is stable in an amount of from 0.1 to 15 wt % in a composition comprising from 10 to 90 wt % ethanol and the microcapsules.

18. The microcapsule of claim 17, wherein the composition is in the form of a perfume, an eau de toilette, an eau de parfum, a cologne or a body splash or a spray.

19. The microcapsule of claim 1, which is stable in an amount of from 0.1 to 15 wt % in a composition comprising from 2 to 50 wt % of at least one surfactant, water and the microcapsules.

20. The microcapsule of claim 19, wherein the composition is in the form of a home- or personal-care product.

* * * * *

UNITED STATES PATENT AND TRADEMARK OFFICE
CERTIFICATE OF CORRECTION

PATENT NO. : 9,849,435 B2
APPLICATION NO. : 15/105487
DATED : December 26, 2017
INVENTOR(S) : Rotello et al.

Page 1 of 1

It is certified that error appears in the above-identified patent and that said Letters Patent is hereby corrected as shown below:

On the Title Page

Item (73) Assignee, after "Firmenich SA, Geneva (CH)", insert -- University of Massachusetts, Boston, MA (US) --.

Signed and Sealed this
Twenty-eighth Day of May, 2019

Andrei Iancu
*Director of the United States Patent and Trademark Office*